(12) United States Patent
Litvak et al.

(10) Patent No.: US 7,447,549 B2
(45) Date of Patent: Nov. 4, 2008

(54) METHODS AND SYSTEMS FOR DENOISING A NEURAL RECORDING SIGNAL

(75) Inventors: Leonid M. Litvak, Los Angeles, CA (US); Abhijit Kulkarni, Newbury Park, CA (US)

(73) Assignee: Advanced Bionioics, LLC, Valencia, CA (US)

( * ) Notice: Subject to any disclaimer, the term of this patent is extended or adjusted under 35 U.S.C. 154(b) by 391 days.

(21) Appl. No.: 11/141,824

(22) Filed: Jun. 1, 2005

(65) Prior Publication Data

US 2006/0276719 A1    Dec. 7, 2006

(51) Int. Cl.
*A61N 1/16*    (2006.01)

(52) U.S. Cl. .......................... 607/55; 607/56

(58) Field of Classification Search .............. 607/55, 607/56, 117; 600/379, 544, 559
See application file for complete search history.

(56) References Cited

U.S. PATENT DOCUMENTS

| | | | |
|---|---|---|---|
| 4,819,647 A | 4/1989 | Byers et al. | |
| 5,193,539 A | 3/1993 | Schulman et al. | |
| 5,193,540 A | 3/1993 | Schulman et al. | |
| 5,312,439 A | 5/1994 | Loeb | |
| 5,501,703 A | 3/1996 | Holsheimer et al. | |
| 5,938,688 A | 8/1999 | Schiff | |
| 6,016,449 A | 1/2000 | Fischell et al. | |
| 6,023,422 A * | 2/2000 | Allen et al. | 365/185.03 |
| 6,051,017 A | 4/2000 | Gerber | |
| 6,052,349 A * | 4/2000 | Okamoto | 369/47.26 |
| 6,129,753 A | 10/2000 | Kuzma | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,219,580 B1 | 4/2001 | Faltys et al. | |
| 6,272,382 B1 | 8/2001 | Faltys et al. | |
| 6,308,101 B1 | 10/2001 | Faltys et al. | |
| 6,381,496 B1 | 4/2002 | Meadows et al. | |
| 6,487,446 B1 | 11/2002 | Hill et al. | |
| 6,516,227 B1 | 2/2003 | Meadows et al. | |
| 6,539,263 B1 | 3/2003 | Schiff et al. | |
| 6,760,626 B1 | 7/2004 | Boveja | |
| 7,082,332 B2 * | 7/2006 | Blamey et al. | 607/57 |
| 2003/0185408 A1 | 10/2003 | Causevic et al. | |

* cited by examiner

*Primary Examiner*—Angela Sykes
*Assistant Examiner*—Joseph Stoklosa
(74) *Attorney, Agent, or Firm*—AdvantEdge Law Group, LLC

(57) ABSTRACT

Methods of denoising a neural recording signal include correlating a neural recording signal with a number of basis functions to obtain a number of weights and then multiplying the weights with the basis functions to obtain a denoised neural recording signal. The basis functions are derived using principal component analysis. Systems for denoising a neural recording signal include one or more devices configured to correlate a neural recording signal with the basis functions to obtain the weights and then multiply the weights with the basis functions to obtain the denoised neural recording signal.

18 Claims, 13 Drawing Sheets

METHODS AND SYSTEMS FOR DENOISING A NEURAL RECORDING SIGNAL

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that acoustic signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce acoustic signals into auditory nerve impulses. Thus, people who suffer from sensorineural hearing loss are unable to derive any benefit from conventional hearing aid systems.

To overcome sensorineural hearing loss, numerous cochlear implant systems—or cochlear prosthesis—have been developed. These devices seek to bypass the hair cells in the cochlea by presenting electrical stimulation directly to the auditory nerve fibers. This leads to the perception of sound in the brain and at least partial restoration of hearing function. To facilitate direct stimulation of the auditory nerve fibers, an array of electrodes may be implanted in the cochlea. A sound processor processes an incoming sound and translates it into electrical stimulation pulses applied by these electrodes which directly stimulate the auditory nerve.

Many cochlear implant systems, as well as other types of neural stimulators, are configured to measure the effectiveness of an electrical stimulation current applied to neural tissue (e.g., the auditory nerve) by using a process known as neural response imaging (NRI). In NRI, the neural stimulator delivers a stimulus to the neural tissue with a stimulating electrode and then records the resulting electrical activity of the neural tissue with a recording electrode. This resulting electrical activity is often referred to as an evoked neural response and occurs when the neural tissue depolarizes in response to the applied stimulus.

An evoked neural response may serve as a diagnostic measure to determine whether the neural stimulator is functioning correctly. NRI may also be used to determine optimal stimulation parameters for each electrode or electrode configuration. For example, NRI may be used to determine the lowest level of stimulating current that is required to evoke a neural response in a particular nerve. This information may then be used to optimize the stimulation parameters or settings of the cochlear implant system. NRI may also be used for a number of additional reasons.

In practice, however, the signal recorded by the recording electrode often includes undesirable signals that interfere with detection of the desired neural response. The terms "neural recording" and "neural recording signal" will be used herein and in the appended claims, unless otherwise specifically denoted, to refer to any signal recorded by the recording electrode. As will be explained in more detail below, a neural recording signal may include any combination of a neural response signal, noise, and/or stimulus artifact. Neural recording signals are sometimes referred to as evoked potential recordings.

As mentioned, a neural recording may include noise. Noise refers to any signal that is not correlated with the stimulus that is applied to the neural tissue by the neural stimulator. Noise is generally unpredictable.

Furthermore, a neural recording may also include stimulus artifact. Stimulus artifact include signals, other than the neural response, that are correlated with the stimulus that is used to evoke the neural response. For example, the stimulus artifact may include the voltage potential of the stimulus pulse itself. Another source of stimulus artifact is cross-talk between the recording circuit and the stimulation circuit.

The presence of noise often makes it difficult to determine whether a neural recording includes a neural response. A number of conventional techniques exist for removing noise from a signal. However, these techniques are often ineffective when applied to a neural recording.

For example, filtering may be used to remove noise that has a different frequency than the frequency of a particular signal of interest. However, in neural stimulation systems, the frequency of the noise and the frequency of an evoked neural response signal are often similar. Thus, conventional filtering cannot always be used to remove noise from a neural recording.

Signal correlation may also be used to remove noise from a signal of interest. In signal correlation, a measured signal is correlated with a known reference signal to remove uncorrelated noise from the measured signal. However, evoked neural responses are often variable from patient to patient. Hence, a single reference signal cannot be used to correlate evoked neural responses from multiple patients. The signal correlation technique is therefore ineffective in many instances in removing noise from a neural recording.

SUMMARY

Methods of denoising a neural recording signal include correlating a neural recording signal with a number of basis functions to obtain a number of weights and then multiplying the weights with the basis functions to obtain a denoised neural recording signal. The basis functions are derived from pre-existing neural recording signals using principal component analysis.

Systems for denoising a neural recording signal include one or more devices configured to correlate a neural recording signal with a number of basis functions to obtain a number of weights and then multiply the weights with the basis functions to obtain a denoised neural recording signal. The basis functions are derived from pre-existing neural recording signals using principal component analysis.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Methods and systems for denoising a neural recording signal that is evoked from neural tissue are described herein. The neural recording is first correlated with a number of basis functions derived using principal component analysis to obtain a number of weights. The weights are then multiplied with the basis functions to obtain a denoised neural recording signal.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
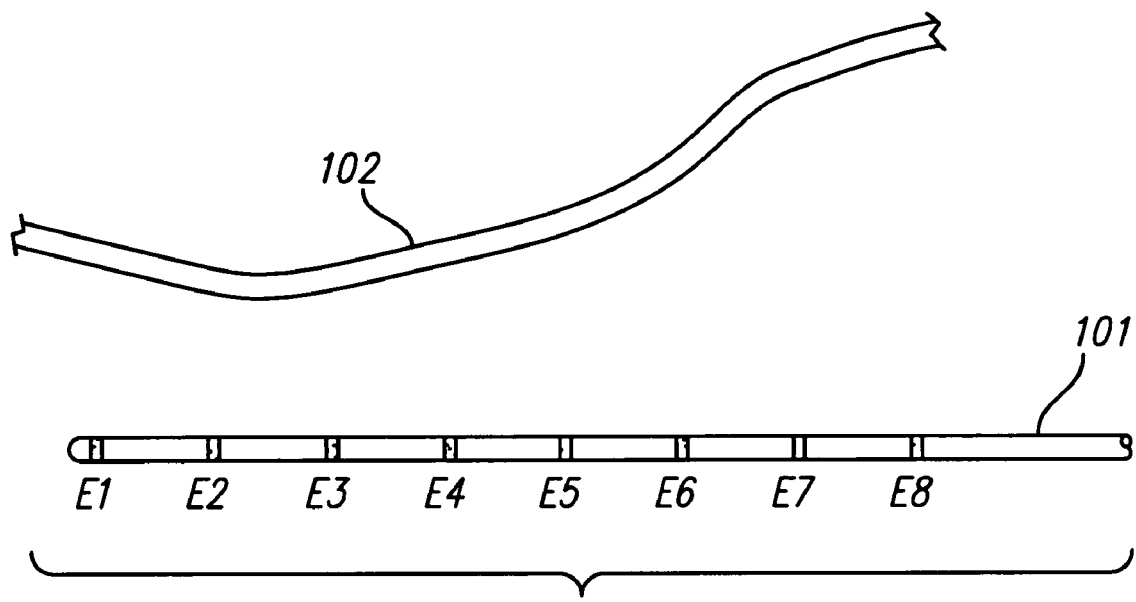
FIG. 1 shows a lead having an electrode array with electrodes E1 through E8 according to principles described herein.

FIG. 1 shows a lead (101) supporting an electrode array with electrodes E1 through E8. The lead (101) may be attached to a neural stimulator (not shown). The stimulator is configured to provide an electrical current via the electrode array to stimulate target tissue, e.g., neural tissue (102). The stimulation current output at each of the electrodes (E1-E8) may be independently controlled by the stimulator. The lead (101) of FIG. 1 includes eight electrodes for illustrative purposes only. It will be recognized that the lead (101) may include any number of electrodes. Furthermore, the electrodes may be arranged in any of a number of configurations. For example, the electrodes may be arranged as an array having at least two or at least four collinear electrodes. In some embodiments, the electrodes are inductively coupled to the stimulator. The lead (101) may be thin (e.g., less than 3 millimeters in diameter) and flexible such that the lead (101) may be readily positioned near target neural tissue (102). Alternatively, the electrodes may be coupled directly to a leadless stimulator.

In some embodiments, each electrode (E1-E8) may be selectively configured to function as a stimulating electrode or a recording electrode as best serves a particular application. For example, E1 may be a used as a stimulating electrode and E2 may be used as a recording electrode. A stimulus, e.g., an electrical stimulation current, may then be applied to the neural tissue (102) via the stimulating electrode E1. The resulting electrical activity of the nerve (102) when the nerve (102) depolarizes in response to the applied stimulus is recorded with the recording electrode E2. As mentioned previously, this electrical activity is referred to as an evoked neural response or simply a neural response.

Figure 2:
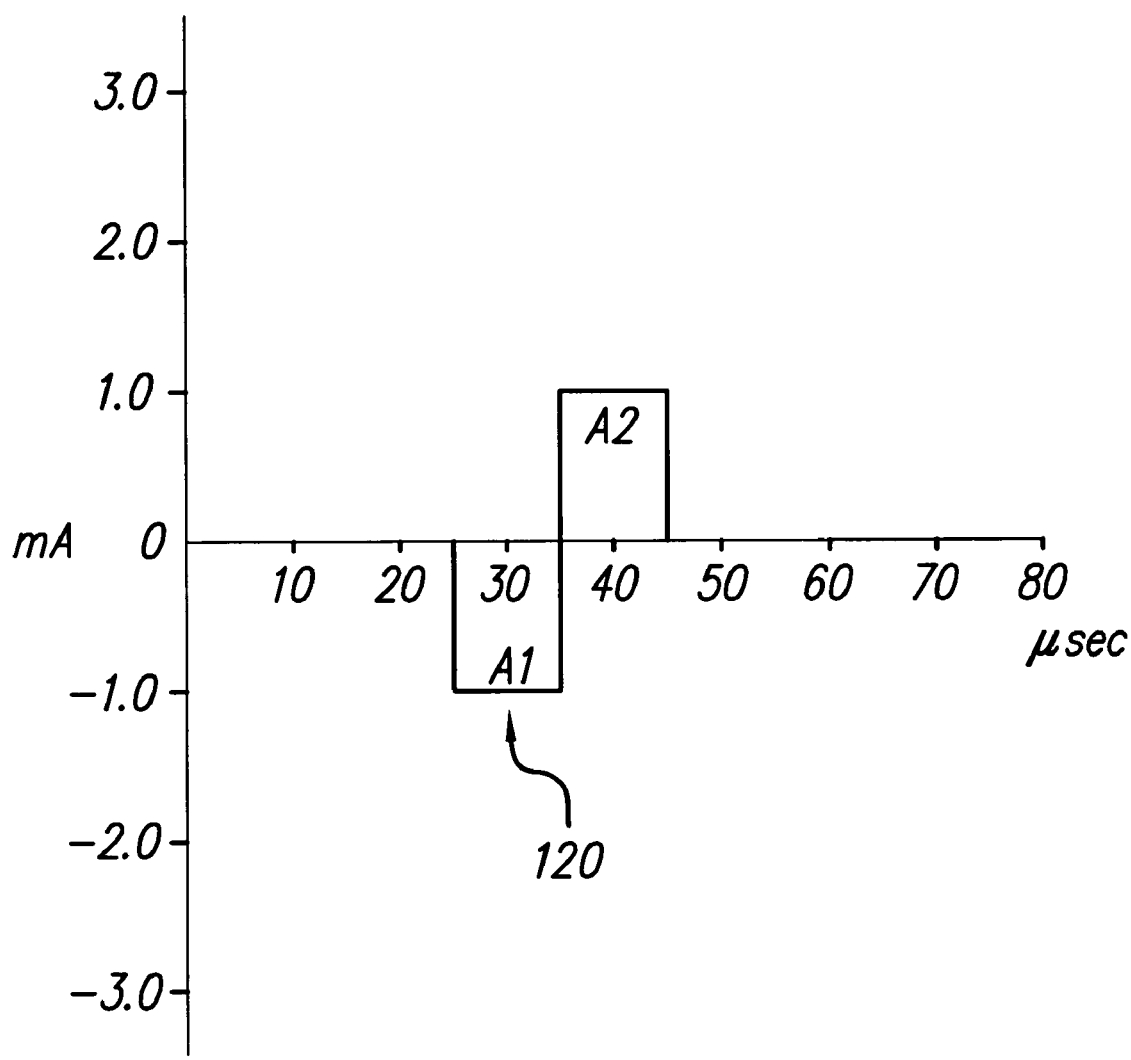
FIG. 2 illustrates an exemplary stimulus that may be delivered to neural tissue via a stimulating electrode according to principles described herein.

FIG. 2 illustrates an exemplary stimulus (120), e.g., an electrical stimulation current pulse that may be delivered to neural tissue via a stimulating electrode. The stimulus (120) of FIG. 2 is biphasic. In other words, the stimulus (120) includes two parts—a negative first phase having an area A1 and a positive second phase having an area A2. It is usually the negative phase that causes neural tissue to depolarize (fire). The biphasic stimulus (120) shown in FIG. 2 has an amplitude of 1 milliamp (ma) and a pulse width of 20 microseconds (μ sec) for illustrative purposes only. It will be recognized that any of the characteristics of the stimulus (120), including, but not limited to, the pulse shape, amplitude, pulse width, frequency, burst pattern (e.g., burst on time and burst off time), duty cycle or burst repeat interval, ramp on time, and ramp off time may vary as best serves a particular application.

The biphasic stimulus (120) shown in FIG. 2 is "charge balanced" because the negative area A1 is equal to the positive area A2. A charge-balanced biphasic pulse is often employed as the stimulus to minimize electrode corrosion and charge build-up which can harm surrounding tissue. However, it will be recognized that the biphasic stimulus (120) may alternatively be charge-imbalanced as best serves a particular application.

In some embodiments, when the amplitude and pulse width of the stimulus (120) of FIG. 2 reach a supra-threshold (i.e., a threshold stimulus large enough to depolarize a target nerve), the voltage gradient at some surface point on the nerve (102; FIG. 1) will be sufficiently negative as to cause the nerve (102; FIG. 1) to depolarize from its resting state and propagate an electrical signal along the length of the nerve (102). The voltage gradient of this electrical signal propagation can be captured with a recording electrode as the evoked neural response of the target nerve.

Before discussing the present methods and systems of obtaining and denoising an evoked neural response signal, it is helpful to understand the components of a number of exemplary neural stimulators in which the present methods and systems may be employed.

Figure 3:
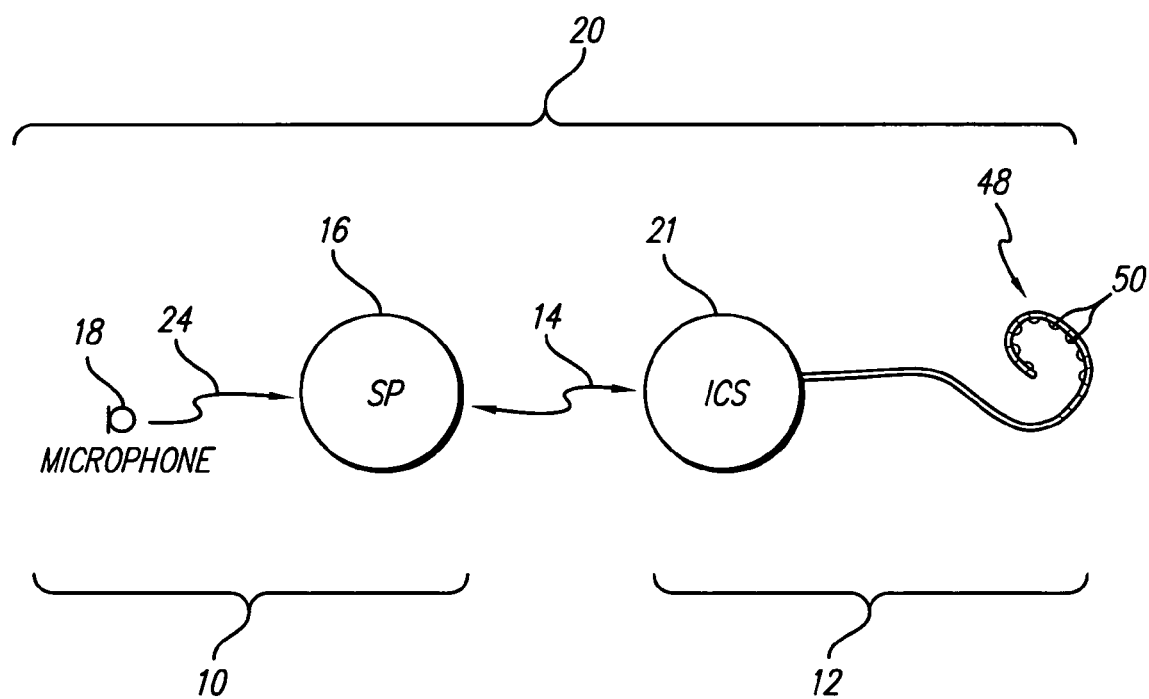
FIG. 3 shows an exemplary cochlear implant system that may be used as a neural stimulator according to principles described herein.

FIG. 3 shows an exemplary cochlear implant system (20) that may be used as a neural stimulator in accordance with the present methods and systems. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties. The cochlear implant system (20) includes a speech processor portion (10) and a cochlear stimulation portion (12). The speech processor portion (10) may include a speech processor (SP) (16), a microphone (18), and/or additional circuitry as best serves a particular application. The cochlear stimulation portion (12) may include an implantable cochlear stimulator (ICS) (21), a number of electrodes (50) arranged in an electrode array (48), and/or additional circuitry as best serves a particular application. The components within the speech processor portion (10) and the cochlear stimulation portion (12) will be described in more detail below.

The microphone (18) of FIG. 3 is configured to sense acoustic signals and convert such sensed signals to corresponding electrical signals. The electrical signals are sent to the SP (16) over an electrical or other suitable link (24). Alternatively, the microphone (18) may be connected directly to, or integrated with, the SP (16). The SP (16) processes these converted acoustic signals in accordance with a selected speech processing strategy to generate appropriate control signals for controlling the ICS (21). These control signals may specify or define the polarity, magnitude, location (i.e., which electrode pair or electrode group receive the stimulation current), and timing (i.e., when the stimulation current is to be applied to a particular electrode pair) of the stimulation current that is generated by the ICS (21).

The electrode array (48) of FIG. 3 is adapted to be inserted within a duct of the cochlea. As shown in FIG. 3, the array (48) includes a multiplicity of electrodes (50), e.g., sixteen electrodes, spaced along its length. Each of the electrodes (50) is individually connected to the ICS (21). The electrode array (48) may be substantially as shown and described in U.S. Pat. Nos. 4,819,647 or 6,129,753, each of which is incorporated herein by reference in its respective entirety. Electronic circuitry within the ICS (21) is configured to apply stimulation current to selected pairs or groups of the individual electrodes (50) included within the electrode array (48) in accordance with a specified stimulation pattern defined by the SP (16).

The ICS (21) and the SP (16) may be electronically connected via a suitable data or communications link (14). In some embodiments, the SP (16) and the microphone (18) comprise an external portion of the cochlear implant system (20) and the ICS (21) and the electrode array (48) comprise an implantable portion of the system (20). In alternative embodiments, one or more portions of the SP (16) are included within the implantable portion of the cochlear implant system (20). The implantable portion of the cochlear implant system (20) is implanted within the patient's body. Thus, the data link (14) is a transcutaneous (through the skin) data link that allows power and control signals to be sent from the SP (16) to the ICS (21). In some embodiments, data and status signals may also be sent from the ICS (21) to the SP (16).

The external and implantable portions of the cochlear implant system (20) may each include one or more coils configured to transmit and receive power and/or control signals via the data link (14). For example, the external portion of the cochlear implant system (20) may include an external coil (not shown) and the implantable portion of the cochlear implant system (20) may include an implantable coil (not shown). The external coil and the implantable coil may be inductively coupled to each other, thereby allowing data to be transmitted between the external portion and the implantable portion. The data may include, for example, the magnitude and polarity of a sensed acoustic signal. The external coil may also transmit power from the external portion to the implantable portion of the cochlear implant system (20). It will be noted that, in some embodiments, both the SP (16) and the ICS (21) may be implanted within the patient, either in the same housing or in separate housings. If the SP (16) and the ICS (21) are in the same housing, the link (14) may be realized with a direct wire connection within such housing. If the SP (16) and the ICS (21) are in separate housings, the link (14) may be an inductive link, for example.

Figure 4:
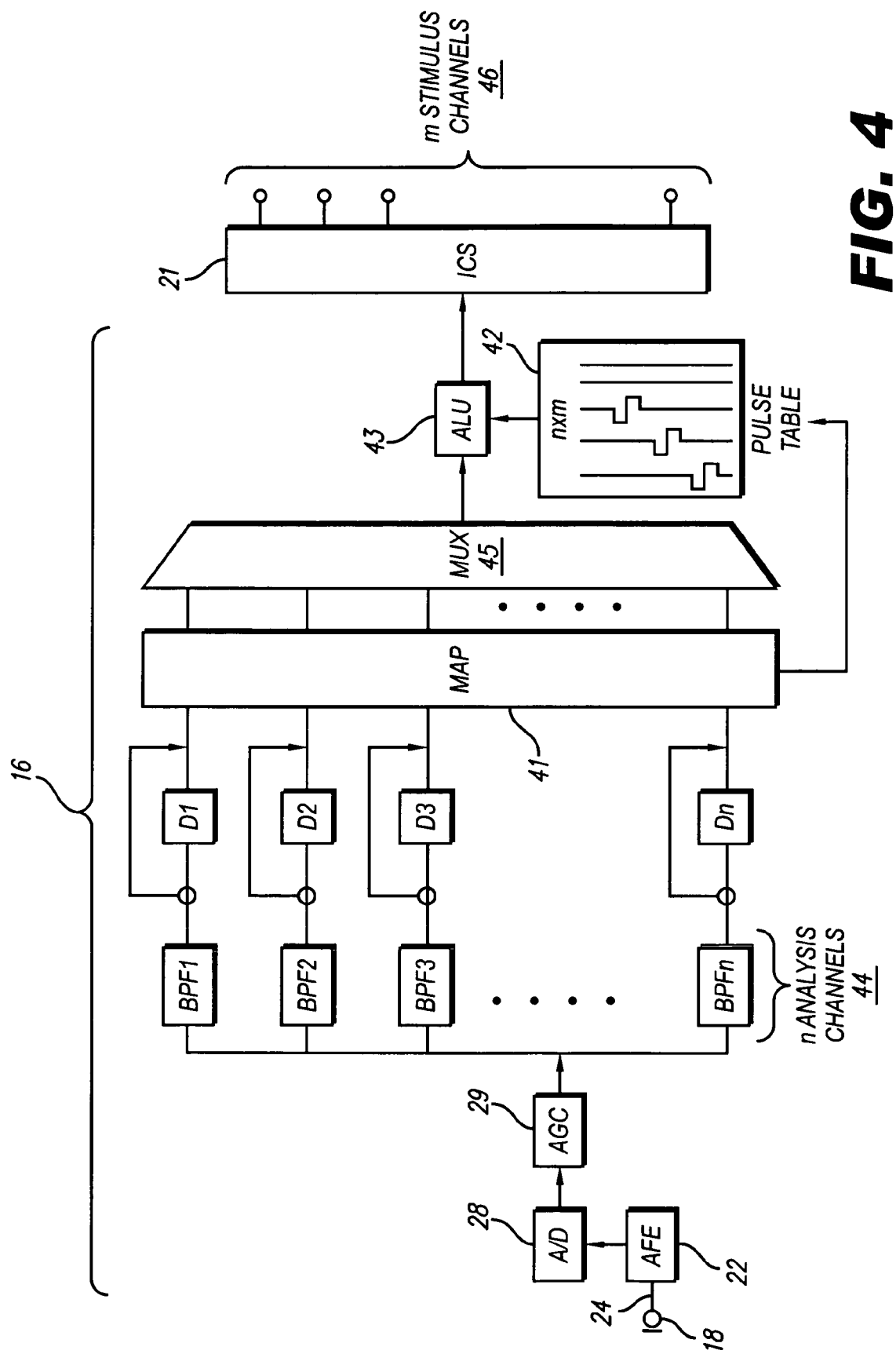
FIG. 4 is a functional block diagram of an exemplary speech processor and an implantable cochlear stimulator according to principles described herein.

FIG. 4 is a functional block diagram of an exemplary SP (16) and ICS (21). The functions shown in FIG. 4 are merely representative of the many different functions that may be performed by the SP (16) and/or the ICS (21). A more complete description of the functional block diagram of the SP (16) and the ICS (21) is found in U.S. Pat. No. 6,219,580, which is incorporated herein by reference in its entirety.

As shown in FIG. 4, the microphone (18) senses acoustic information, such as speech and music, and converts the acoustic information into one or more electrical signals. These signals are then amplified in audio front-end (AFE) circuitry (22). The amplified audio signal is then converted to a digital signal by an analog-to-digital (A/D) converter (28). The resulting digital signal is then subjected to automatic gain control using a suitable automatic gain control (AGC) function (29).

After appropriate automatic gain control, the digital signal is then processed in one of a number of digital signal processing or analysis channels (44). For example, the SP (16) may include, but is not limited to, eight analysis channels (44). Each analysis channel (44) may respond to a different frequency content of the sensed acoustical signal. In other words, each analysis channel (44) includes a band-pass filter (BP1-BPFn) or other type of filter such that the digital signal is divided into n frequency channels. The lowest frequency filter may be a low-pass filter, and the highest frequency filter may be a high-pass filter.

As shown in FIG. 4, each analysis channel (44) may also include a detection stage (D1-Dn). Each detection stage (D1-Dn) may include an energy detection circuit (not shown), which may be realized, e.g., through a rectification circuit followed by an integrator circuit. As shown in FIG. 4, each of the detection stages (D1-Dn) may alternatively be bypassed depending on the particular signal processing strategy being used.

After energy detection, or bypassing of such, the signal from each of the n analysis channels (44) is forwarded to a mapping stage (41). The mapping stage (41) may be configured to map the signals in each of the analysis channels (44) to one or more of the m stimulus channels (46). The mapping stage (41) may be further configured to perform additional processing of the signal, such as signal compression. The signals output by each analysis channel (44) may then be serialized by a multiplexer (45) into one serial data channel. The multiplexed signal may then be further processed according to information included in a pulse table (42) connected to an arithmetic logic unit (ALU) (43). After the signal is appropriately processed, compressed, and mapped, the signal may be input into the ICS (21) to control the actual stimulus patterns that are applied to the patient via the electrode array (48; FIG. 3).

As mentioned, each of the n analysis channels (44) may be mapped to one or more stimulus channels (46). In other words, the information contained in the n analysis channels (44) controls the stimulus patterns that are applied to the patient by the ICS (21) and its associated electrode array (48; FIG. 3). Stimulus current may be applied to any number of stimulation sites within the patient's cochlea via the m stimulus channels (46). As used herein and in the appended claims, the term "stimulation site" will be used to refer to a target area or location at which the stimulus current is applied. For example, a stimulation site may refer to a particular location in the neural tissue of a cochlear implant patient. Through appropriate weighting and sharing of currents between the electrodes (50; FIG. 3), stimulus current may be applied to any stimulation site along the length of the electrode array (48; FIG. 3).

Figures 5A, 5B:
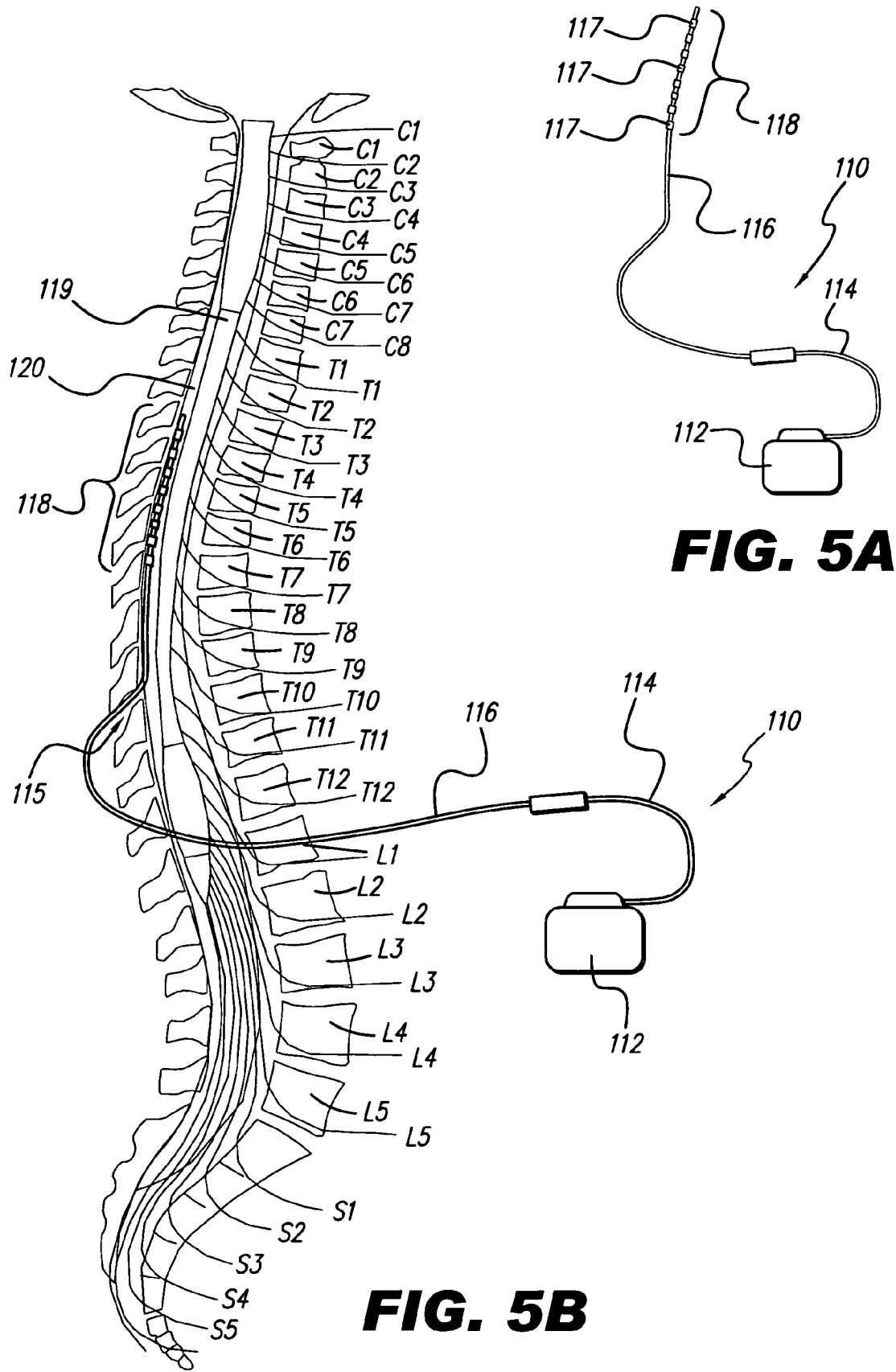
FIGS. 5A and 5B show a spinal cord stimulator (SCS) system that may be used as a neural stimulator according to principles described herein.

FIGS. 5A and 5B show a spinal cord stimulator (SCS) system (110) that may be used as a neural stimulator in accordance with the present methods and systems. The SCS (110) may be used to treat a number of different medical conditions such as, but not limited to, chronic pain.

As shown in FIG. 5A, the SCS (110) may include an implantable pulse generator (IPG) (112), a lead extension (114), and an electrode lead (116) having an electrode array (118) thereon. The electrode array (118) includes a plurality of electrodes (117). The electrodes (117) may be arranged, as shown in FIG. 5A, in an in-line array near the distal end of the lead (116). Other electrode array configurations may also be used. The lead extension (114) need not always be used with the SCS (110), but may be used depending on the physical distance between the IPG (112) and the stimulation site within the patient. The IPG (112) is configured to generate stimulation current pulses that are applied to a stimulation site via one or more of the electrodes (117). Exemplary spinal cord stimulators suitable for use as described herein include, but are not limited to, those disclosed in U.S. Pat. Nos. 5,501,703; 6,487,446; and 6,516,227, all of which are incorporated herein by reference in their respective entireties.

FIG. 5B shows that the electrode array (118) of the SCS (110) may be implanted in the epidural space (120) of a patient in close proximity to the spinal cord (119). Because of the lack of space near the lead exit point (115) where the electrode lead (116) exits the spinal column, the IPG (112) is generally implanted in the abdomen or above the buttocks. However, it will be recognized that the IPG (112) may be implanted in any suitable implantation site. The lead extension (114) facilitates implanting the IPG (112) at a location that is relatively distant from the lead exit point (115).

The cochlear implant system (20; FIG. 3) and the SCS (110; FIG. 5A) are merely illustrative of many types of neural stimulators that may be used to perform NRI. For example, the neural stimulator may additionally or alternatively include an implantable pulse generator (IPG) coupled to one or more leads having a number of electrodes, a deep brain stimulator, an implantable microstimulator, an external stimulator, or any other type of stimulator configured to perform NRI. Exemplary IPGs suitable for use as described herein include, but are not limited to, those disclosed in U.S. Pat. Nos. 6,381,496, 6,553,263; and 6,760,626. Exemplary deep brain stimulators suitable for use as described herein include, but are not limited to, those disclosed in U.S. Pat. Nos. 5,938,688; 6,016,449; and 6,539,263. Exemplary implantable microstimulators, such as the BION® microstimulator (Advanced Bionics® Corporation, Valencia, Calif.), suitable for use as described herein include, but are not limited to, those disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

As mentioned, it is often desirable to deliver a stimulus to neural tissue with a stimulating electrode and then record the resulting electrical activity of the neural tissue with a recording electrode. This resulting electrical activity is referred to as an evoked neural response or simply, a neural response, and occurs when the neural tissue depolarizes in response to the applied stimulus.

For example, in a normal ear, a single auditory nerve fiber or cell generates an action potential when the cell's membrane is depolarized to a threshold value, after which a spike occurs. Sodium ions entering the cell make the inside of the cell more positive, that is, depolarized. In some embodiments, an electrical stimulation current may be used to depolarize the nerve cell. This depolarization effect can be likened to taking a photograph by pressing the shutter button on a camera. Pressing on the button has no effect until it crosses a threshold pressure, and then "click"—the shutter opens and the film is exposed. In the same way, depolarizing a neuron has no effect until the depolarization reaches a threshold, and then, all at once, an action potential is generated.

Figure 6C:
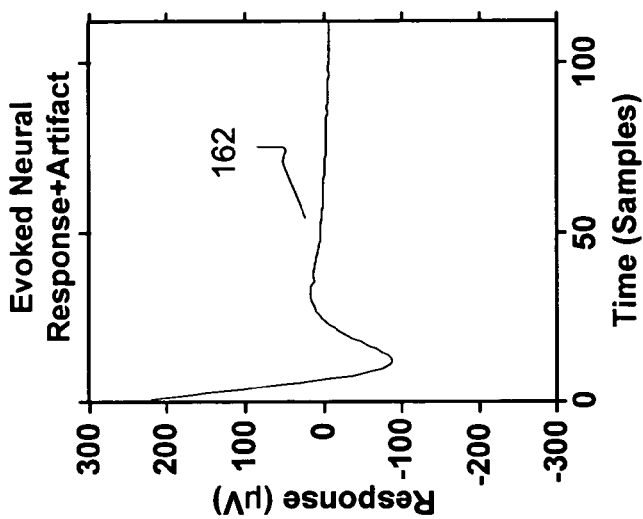
FIG. 6C is a graph depicting an exemplary neural recording signal according to principles described herein.

The evoked neural response as recorded by the recording electrode includes a sum of action potentials of a number of nerve cells. FIG. 6A is a graph depicting an exemplary evoked neural response signal (160). As shown in FIG. 6A, the horizontal axis represents time in samples and the vertical axis represents the amplitude of the response in microvolts (μV). As shown in FIG. 6A, the evoked neural response signal (160) is typically characterized by a first negative peak (N1) followed by a first positive peak (P1). It will be recognized that evoked neural responses differ in timing and amplitude from patient to patient.

Unfortunately, the recording electrode may additionally or alternatively record noise and/or stimulus artifact. In general, a neural recording may include any combination of a neural response signal, noise, and/or stimulus artifact. In some instances, the neural recording obtained by the recording electrode only includes stimulus artifact and noise. For example, if the stimulus pulse is too low to trigger depolarization of the nerve (102), the nerve (102) will not produce a neural response and the recording electrode will only record the stimulus artifact and any noise that is present.

Figure 6B:
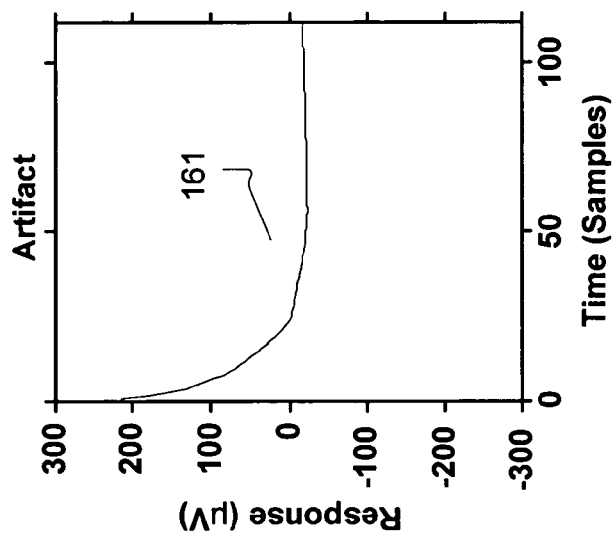
FIG. 6B is a graph depicting an exemplary artifact signal according to principles described herein.
Figure 6A:
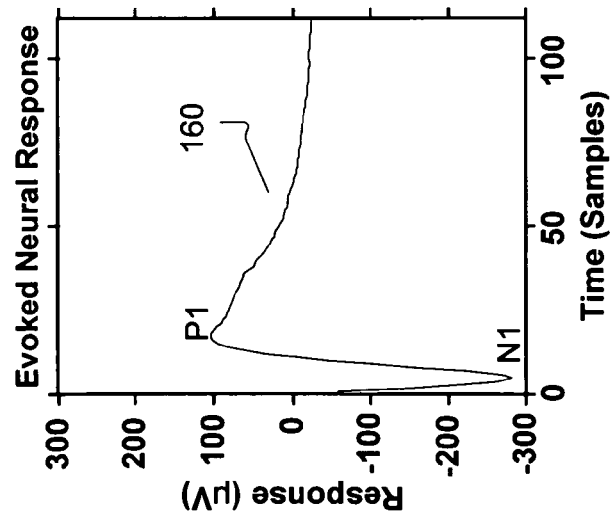
FIG. 6A is a graph depicting an exemplary evoked neural response signal according to principles described herein.

FIG. 6B is a graph depicting an exemplary artifact signal (161). The artifact signal (161) is typically characterized as a sum of two decaying exponentials, one with a fast time constant and one with a slow time constant.

FIG. 6C is a graph depicting a neural recording signal (162) that includes both the evoked neural response signal (160) of FIG. 6A and the artifact signal (161) of FIG. 6B. As shown in FIG. 6C, the neural recording (162) is a sum of the evoked neural response signal (160; FIG. 6A) and the artifact signal (161; FIG. 6B).

Figure 7A:
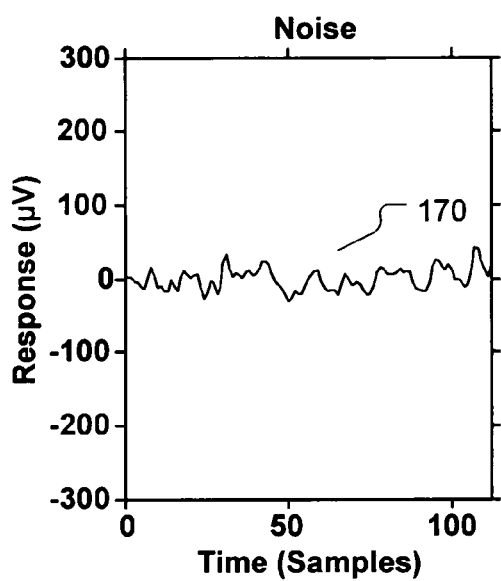
FIG. 7A is a graph depicting an exemplary noise signal according to principles described herein.

As mentioned previously, the neural recording obtained by a recording electrode may also include noise. Noise refers to any signal that is not correlated with the stimulus pulse and is generally unpredictable. FIG. 7A is a graph depicting an exemplary noise signal (170) that may be recorded by the recording electrode. Because the noise signal (170) is unpredictable, the noise signal (170) may have any frequency or amplitude.

Figure 7B:
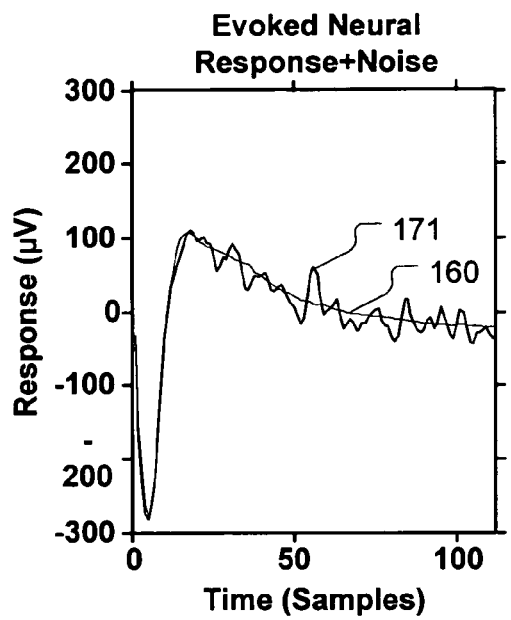
FIG. 7B is a graph depicting the effect of the noise signal of FIG. 7A on the evoked neural response signal of FIG. 6A according to principles described herein.
Figure 7C:
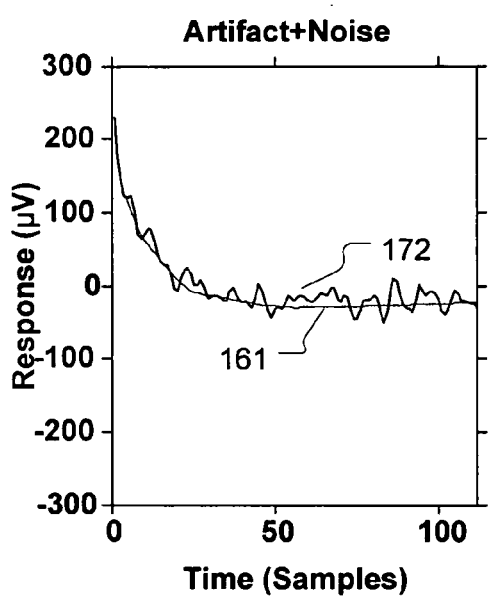
FIG. 7C is a graph depicting the effect of the noise signal of FIG. 7A on the artifact signal of FIG. 6B according to principles described herein.
Figure 7D:
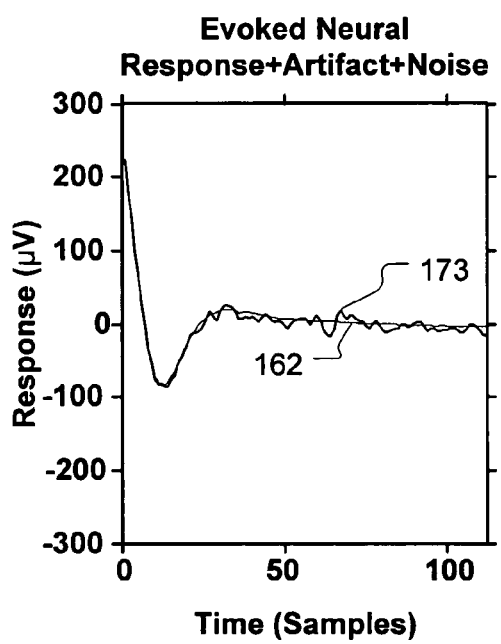
FIG. 7D is a graph depicting the effect of the noise signal of FIG. 7A on the neural recording signal of FIG. 6C according to principles described herein.

FIGS. 7B-7D are graphs depicting the effect (171) of the noise signal (170; FIG. 7A) on the evoked neural response signal (160) of FIG. 6A, the effect (172) of the noise signal (170; FIG. 7A) on the artifact signal (161) of FIG. 6B, and the effect (173) of the noise signal (170; FIG. 7A) on the neural recording signal (162) of FIG. 6C, respectively.

It is often desirable to denoise or decrease the effect of the noise on a neural recording signal containing a neural response and/or stimulus artifact. An exemplary method of denoising a neural recording signal will now be described in connection with the flow chart shown in FIG. 8. The term "denoising" will be used herein and in the appended claims, unless otherwise specifically denoted, to refer to decreasing or removing noise from a neural recording signal. The method may be used in connection with any type of neural stimulator. The steps shown in FIG. 8 and described below may be modified, reordered, removed, and/or added to as best serves a particular application.

Figure 8:
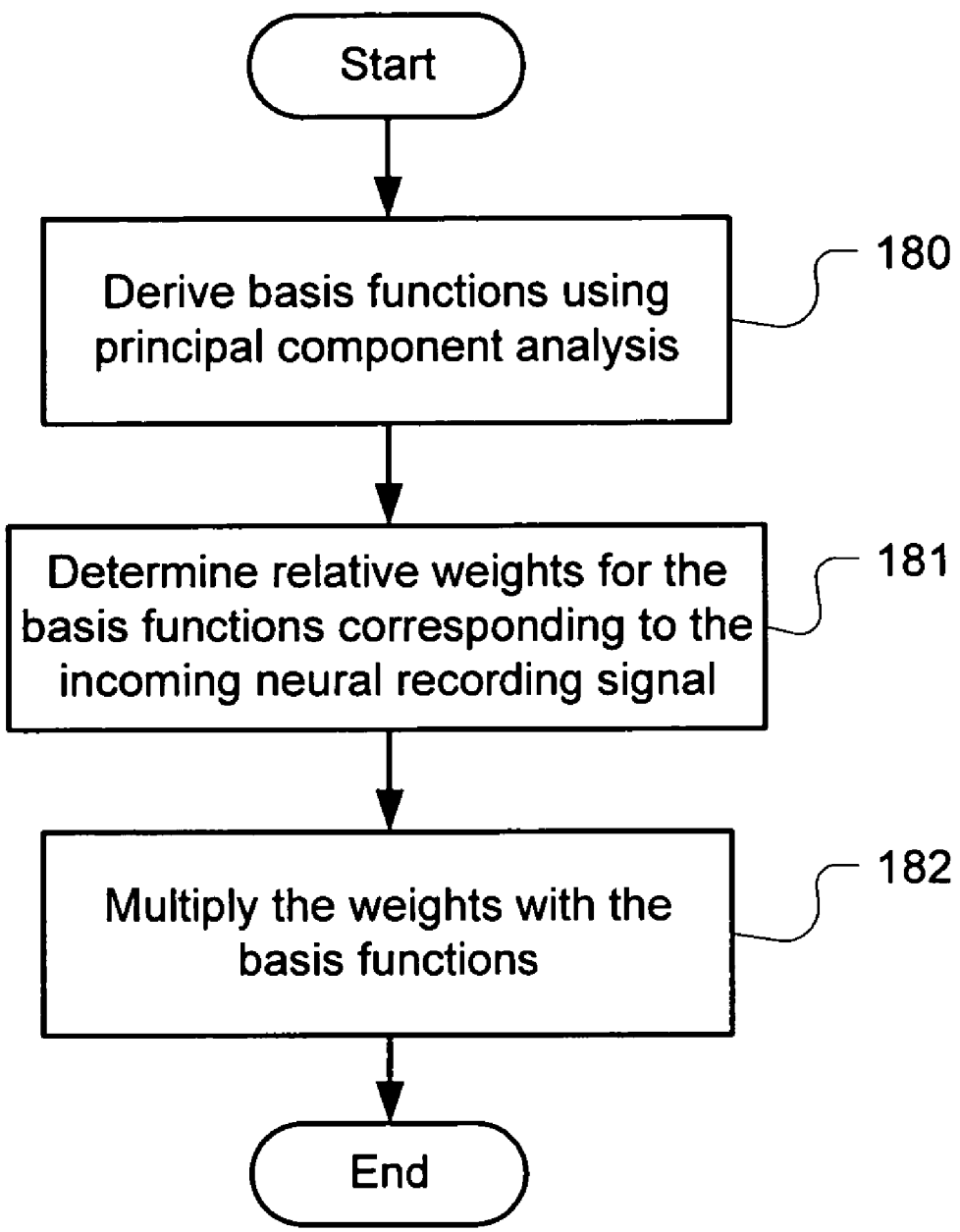
FIG. 8 is a flow chart illustrating an exemplary method of denoising a neural recording signal according to principles described herein.

As shown in FIG. 8, a number of basis functions are first derived using principal component analysis to describe a set of previously collected neural recording signals (step 180). In some embodiments, step 180 is performed only once, and not every time a neural recording signal is denoised. Principal component analysis is a statistical technique used to derive a number of functions that, when summed together, describe a given set of data. These functions are often referred to as basis functions or principal components, both of which terms will be used interchangeably herein and in the appended claims unless otherwise specifically denoted.

An example of deriving a number of basis functions that describe a set of neural recording signals corresponding to the auditory nerve will now be given. It will be recognized that the following example is merely illustrative and that the neural recording signal may be evoked in response to stimulus applied to any neural tissue by any neural stimulator.

A large number of neural recording signals were evoked and recorded by audiologists over a period of time. Each measured waveform was computed by averaging the response to a cathodic-anodic and anodic-cathodic stimulus pulse. A two-point averaging filter was then applied to the data. In addition, synchronized noise was measured by recording the response to stimulation with zero current. The synchronized noise was then subtracted from the response to the cathodic-anodic and anodic-cathodic stimulus pulse.

The evoked neural recording signals were then collected into a measurement matrix $M=[m_1 \ldots m_{8000}]$. As used herein and in the appended claims, unless otherwise specifically denoted, bold capital letters will be used to refer to matrices and bold lower-case letters will be used to refer to vectors. Hence, M is a matrix containing 8,000 measured neural recording signals $m_1$ through $m_{8000}$. Although M contains 8,000 measured neural recording signals in the present example, it will be recognized that M may contain any number of measured neural recording signals as best serves a particular application.

Eigenvalue decomposition was then used to compute the principal components of M. MATLAB™ or any other mathematical tool may be used to perform the eigenvalue decomposition. First, the covariance matrix $C_M = COV(M')$ was computed. A vector of eigenvalues ($\lambda$) and a matrix of eigenvectors arranged in columns ($V_{full}$) were then computed. The matrix $V_{full}$ contains the full components that account entirely for the measurement matrix M.

Because the covariance matrix $C_M$ is symmetric, the eigenvectors within the matrix $V_{full}$ are orthogonal. The eigenvectors within the matrix $V_{full}$ may be normalized to have a norm of one.

Figure 9:
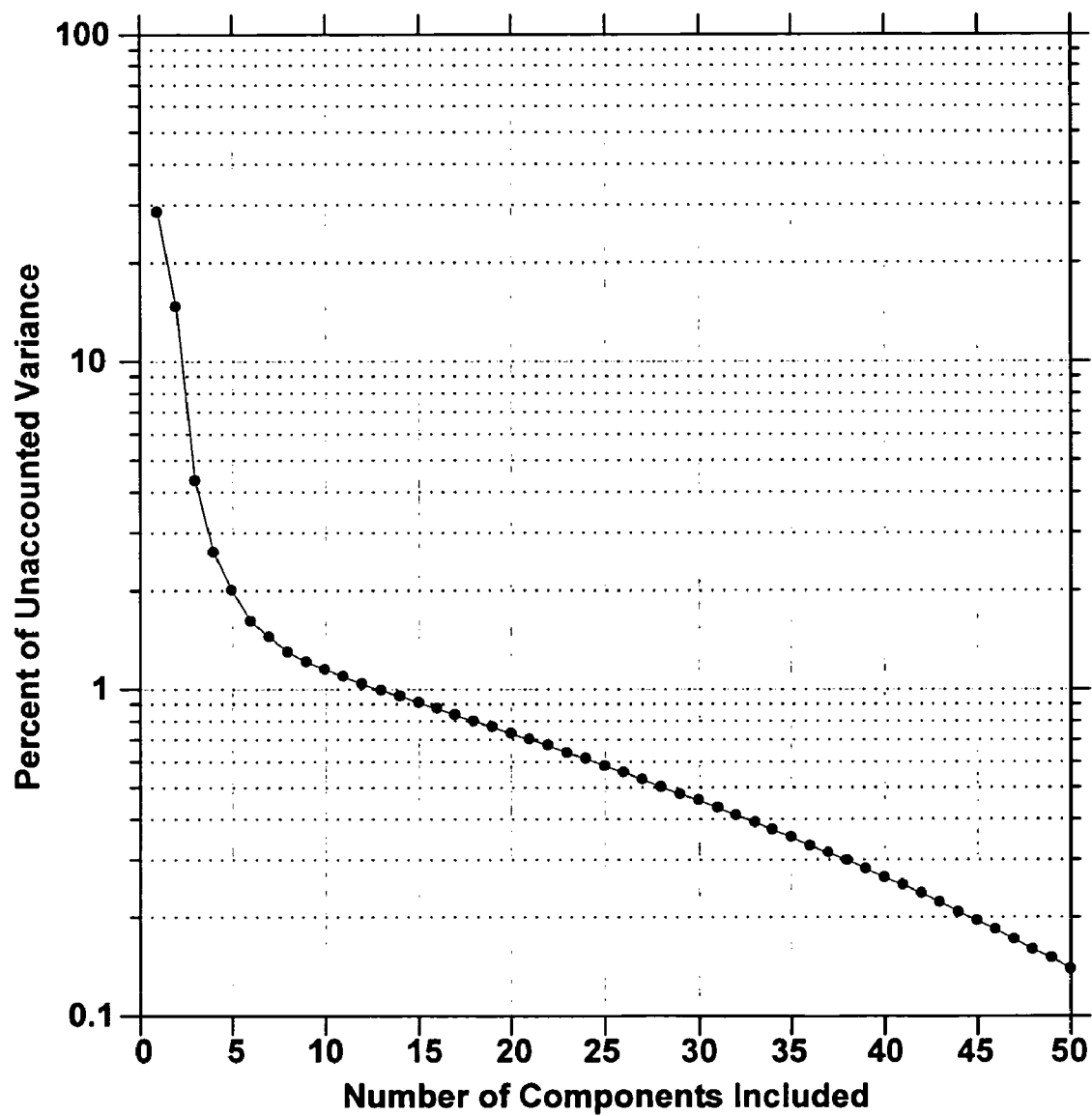
FIG. 9 is a graph showing the percent of unaccounted variance in a matrix of evoked neural recording signals as a function of number of components according to principles described herein.

Although $V_{full}$ contains the full components that account entirely for the data contained in measurement matrix M, it can be shown that a lesser number of these components may sufficiently account for the data in M. FIG. 9 is a graph showing the percent of unaccounted variance in M as a function of the number of components. As shown in FIG. 9, the percent of unaccounted variance decreases as more components are included. However, as shown in FIG. 9, a small number of components (e.g., 5 to 10 components) may account for approximately 98 to 99 percent of the variance.

Figure 10:
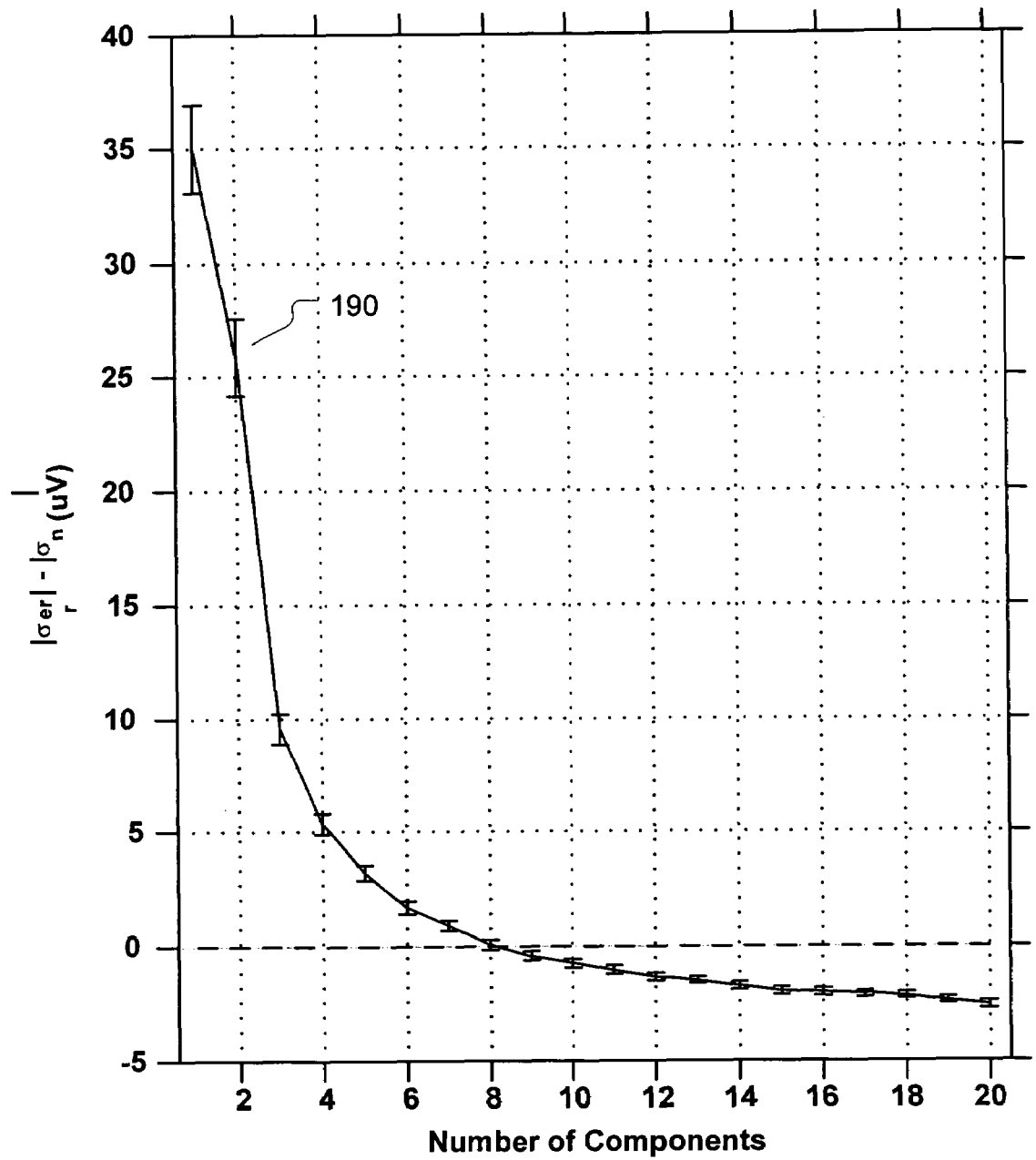
FIG. 10 is a graph illustrating the difference of standard deviations of the errors in the beginning versus in the end of the waveforms in the matrix of evoked neural recording signals as a function of the number of components included according to principles described herein.

FIG. 10 is a graph illustrating the difference of standard deviations of the errors in the beginning versus in the end of the waveforms in M as a function of the number of components included. The error bars (e.g., 190) are approximately 99 percent confidence intervals around the mean estimate of the error. As shown in FIG. 10, the difference becomes zero for eight components. For higher numbers of components, some noise is captured in the measurements. Hence, the error in the beginning portion of the stimulus is less than the standard of deviation.

The results shown in FIGS. 9 and 10 may be used to determine an optimal number of basis functions or components for a given application. For example, seven components capture approximately 98.6 percent of the variance in the data and have a 2 µV mean difference. Thus, seven components are sufficient for many different applications. The examples given herein will use seven components or basis functions. However, it will be recognized that any number of basis functions may be chosen to represent the set of evoked neural recording signals in M.

Figure 11:
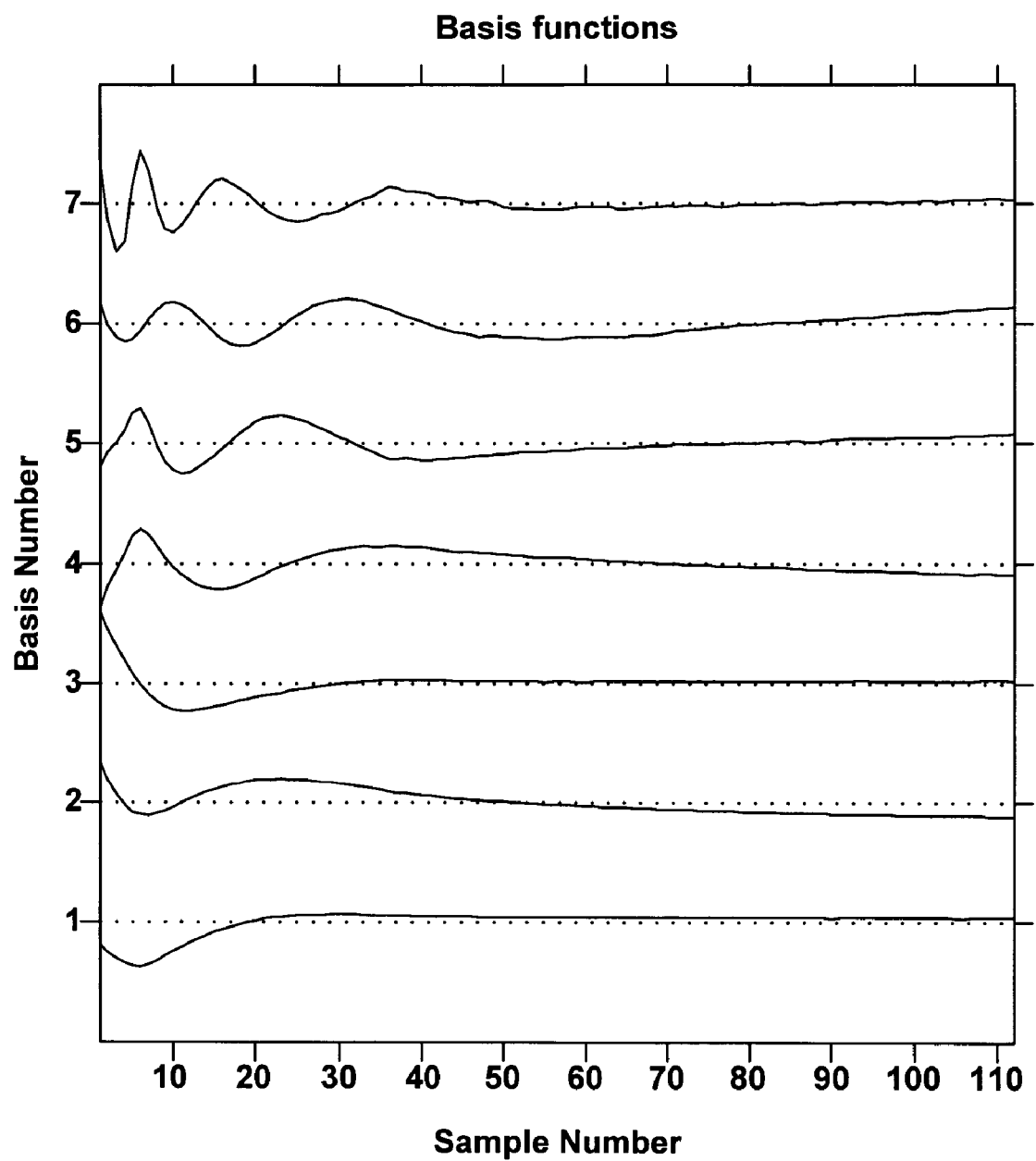
FIG. 11 is a graph showing seven basis functions or components according to principles described herein.

FIG. 11 is a graph showing seven basis functions or components. As shown in FIG. 11, the top basis function (basis function number 7) looks like a neural response signal. The remaining basis functions account for differences in the evoked neural recording signals in M. For purposes of the present example, the seven basis functions or components will be represented by the component matrix $V=[v_1 \ldots v_7]$, where $v_1$ through $v_7$ are vectors representing the seven basis functions. As will be described in more detail below, the component matrix V may be used to denoise an incoming neural recording signal.

Returning to the flow chart of FIG. 8, once the component matrix V has been determined, the next step is to determine relative weights for the basis functions $v_1$ through $v_7$ corresponding to an incoming neural recording signal (step 181). In other words, the amount of each basis function $v_1$ through $v_7$ that is present in the incoming neural recording signal is determined. A computer, digital signal processor (DSP), or any other suitable device may be used to determine the relative weights for the basis functions. As will be described in more detail below, the incoming neural recording signal is denoised by multiplying the weights with the basis functions $v_1$ through $v_7$.

For example, assume that the incoming neural recording signal is represented by m. The relative weights for the basis functions $v_1$ through $v_7$ are determined by correlating the incoming neural recording signal m with the basis functions in the component matrix V. Hence, the weights are equal to V' m.

As shown in FIG. 8, the weights are then multiplied with the basis functions to denoise the incoming neural recording signal (step 182). Thus, the denoised neural recording signal, $m_{denoised}$, is equal to V V' m. For ease of explanation, $M_{denoised} = T m$, where T is the denoising matrix equal to V V'. A computer, digital signal processor (DSP), or any other suitable device may be used to multiply the weights with the basis functions.

Mathematically, the denoising effect of multiplying the weights with the basis functions can be shown by the following equations. Suppose that the incoming neural recording signal is m=s+n, where s represents the evoked neural response signal and/or artifact signal and n represents the uncorrelated noise. Without loss of generality, it can be assumed that n has a zero mean. The denoised waveform is then $m_{denoised}$=T m=T s+T n=$s_{denoised}$+T n. Therefore, the uncorrelated noise in the denoised waveform is $n_{denoised}$=$m_{denoised}$−$s_{denoised}$=T n.

Conceptually, the denoising effect of multiplying the weights with the basis functions can be illustrated by the following example. Suppose that there is only one basis function and the incoming neural recording only contains noise. When this incoming noise is correlated with the basis function, the resulting weight value is low, indicating that the noise does not correlate with the basis function. When the low weight number is multiplied with the basis function, the resulting signal is characterized by a smaller magnitude than the incoming noise signal.

On the other hand, suppose that the incoming neural recording is noiseless. Therefore, when the incoming neural recording signal is correlated with the single basis function, the resulting weight number is high, indicating that the incoming neural recording signal correlates with the basis function. When the high weight number is multiplied with the basis function, the resulting signal is characterized by a magnitude that is relatively close to the magnitude of the incoming neural recording signal.

Figure 12:
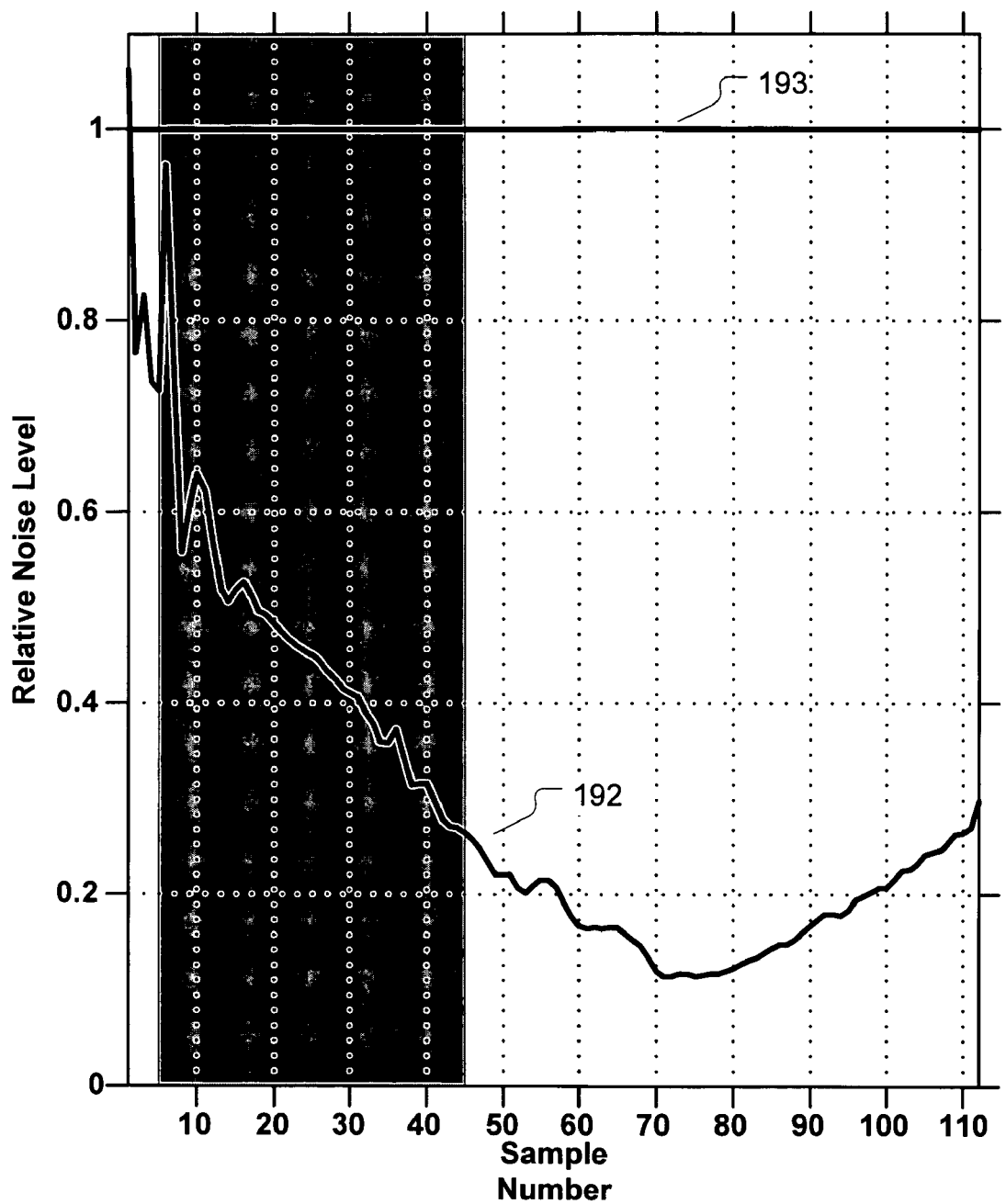
FIG. 12 is a graph showing the amount by which noise is reduced for each point of the waveform representing the incoming neural recording signal according to principles described herein.

The residual noise after denoising can be described by the covariance matrix $CD_n$=E[n n']=T E[n n']T'=T $C_n$T'. The diagonal of the matrix $CD_n$ is the variance at any point. Therefore, the square root of the diagonal is equal to the standard deviation at any given point. Assuming that the incoming noise is white, with unity variance, the decrease in the noise standard deviation is shown in FIG. 12. FIG. 12 shows, as a function of sample number, the amount by which noise is reduced for each point of the waveform representing the neural recording. The horizontal line (193) represents the noise level of the incoming neural recording before denoising. The line (192) represents the noise level of the incoming neural recording signal after denoising. The shaded area represents the range of time where most of the response energy is maximal. In this area, as shown in FIG. 12, an average reduction in noise of nearly 50 percent is achieved by the denoising technique described herein.

In some embodiments, greater noise reductions may be achieved by including fewer components. However, the cost of including fewer components may be loss of some energy in the denoised signal.

The denoising method described in connection with FIG. 8 can be shown to be optimal in a sense that any further filtering that preserves the neural response signal entirely does not improve the signal-to-noise ratio. To demonstrate this, consider a filter F for which F' s=s, for any s, i.e. this filter will not change the neural response and/or artifact component of the neural recording signal at all. Thus, the filtered response is rdf=F' T s+F' T n. However, if V captures all possible responses s, then by necessity F'V=V. In this case, $CD_{nf}$=$CD_n$ and the noise matrix is not changed.

It is often desirable to determine the minimum stimulation current level needed to evoke a neural response. The neural stimulator may then be configured to apply effective, comfortable, and optimal stimulus levels that conserve the power available to the stimulator. However, when the neural recording is marred by noise, it is often difficult to distinguish between a neural recording signal that includes an evoked neural response signal and a neural recording signal that does not include an evoked neural response signal. As used herein and in the appended claims, the term "non-response neural recording signal" will be used to refer to a neural recording signal that does not include an evoked neural response. A non-response neural recording signal may still include artifact and/or noise signals.

Figure 13A:
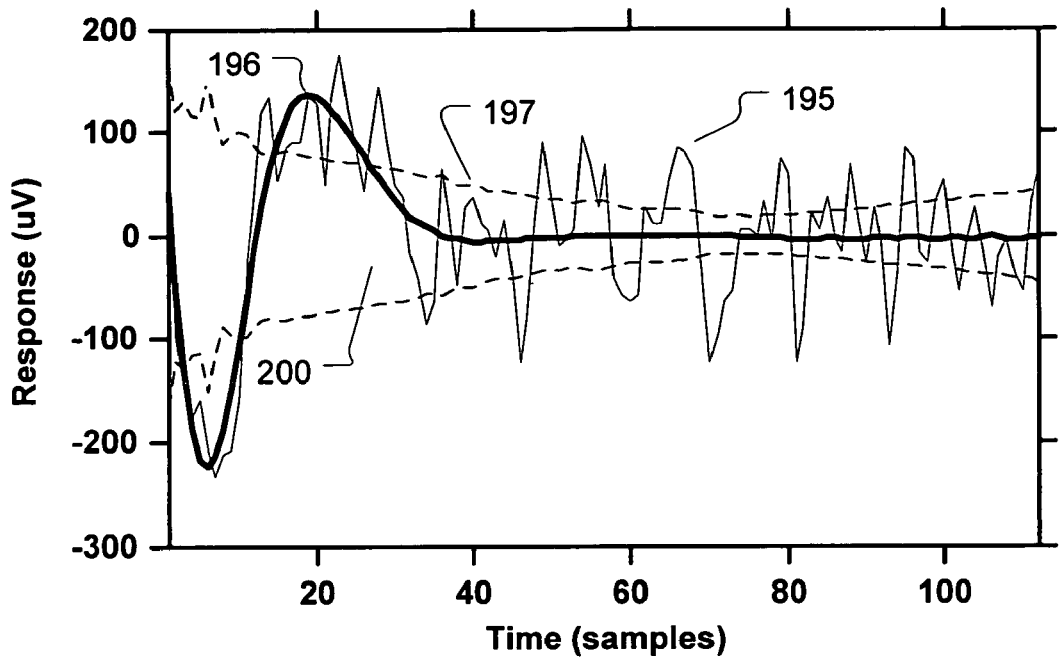
FIGS. 13A and 13B are graphs illustrating a confidence interval that assists in identifying a neural recording signal that includes an evoked neural response signal according to principles described herein.
Figure 13B:
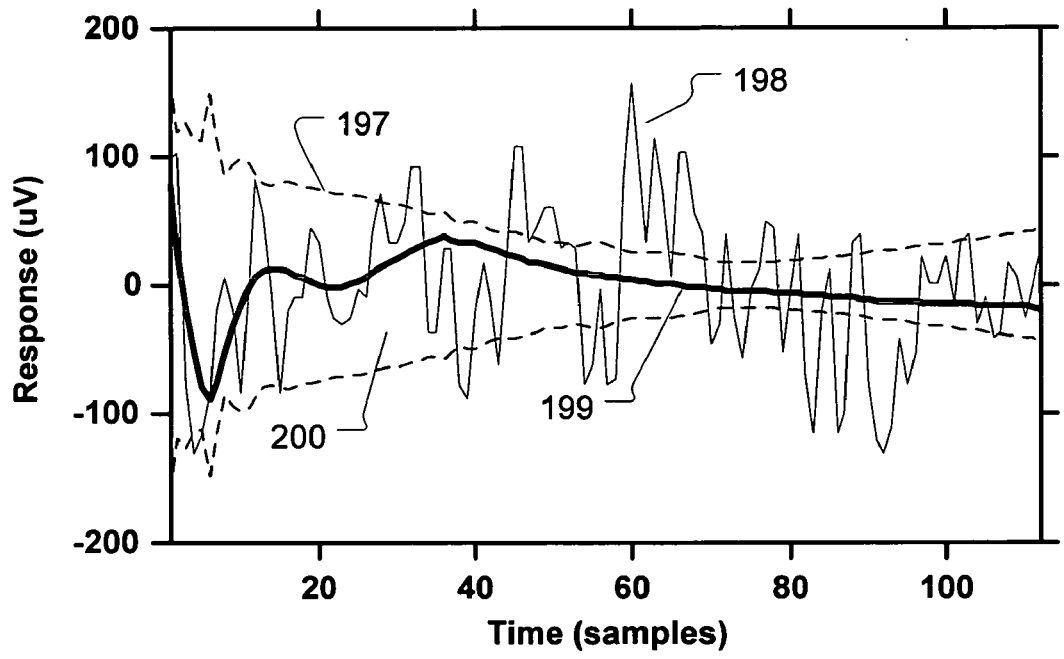

FIGS. 13A and 13B illustrate an exemplary embodiment wherein a confidence interval (200) assists in identifying a neural recording signal that includes an evoked neural response signal. The confidence interval (200) may be derived from any combination of a number of contributing factors including, but not limited to, estimates of noise levels, relative noise levels before and after multiplying the weights with the basis functions, and other factors. As shown in FIGS. 13A and 13B, the confidence interval (200) is indicated by the dashed lines (197) and forms an envelope. As will be explained in more detail below, if the amplitude of a denoised neural recording signal exceeds the confidence interval (200), it is marked as including an evoked neural response signal. Conversely, if the amplitude of the denoised neural recording signal does not exceed the confidence interval (200), it is marked as a non-response neural recording signal.

For example, FIG. 13A shows a neural recording signal prior to denoising (195) and after denoising (196). As shown in FIG. 13A, the amplitude of the denoised signal (196) exceeds the confidence interval (200) and can therefore be marked as including an evoked neural response signal. The denoised signal (196) is smoother than is the signal (195) containing noise and is therefore easier to identify as representing an evoked neural response.

Likewise, FIG. 13B shows a neural recording signal prior to denoising (198) and after denoising (199). As shown in FIG. 13B, the amplitude of the denoised signal (199) does not exceed the confidence interval (200) and therefore may be identified as representing a non-response on the part of the nerve to the applied stimulus. However, as shown in FIG. 13B, the signal (198) containing noise is more difficult to analyze and recognize as being a non-response neural recording signal. For example, a number of negative and positive peaks of the signal (198) containing noise exceed the confidence interval (200). Without denoising this signal (198), it could be mistakenly identified as representing a valid evoked neural response.

In some embodiments, a clinician or other person visually determines whether a neural recording includes an evoked neural response or whether the neural recording is a non-response neural recording signal. Alternatively, the neural stimulator, a computer, or some other device is configured to automatically distinguish between a neural recording that includes an evoked neural response and one that does not.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of denoising a neural recording signal, said method comprising:
    applying a stimulus pulse to neural tissue to generate a neural recording signal;
    correlating said neural recording signal with one or more basis functions derived using principal component analysis to produce one or more weights; and
    multiplying said weights with said basis functions to obtain a denoised neural recording signal.

2. The method of claim 1, wherein said one or more basis functions comprises at least two basis functions and less than or equal to seven basis functions.

3. The method of claim 1, further comprising:
   collecting a plurality of neural recording signals $m_1$ through $m_n$ into a measurement matrix M; and
   using said principal component analysis to derive a matrix $V_{full}$ that comprises a complete set of basis functions that account entirely for said measurement matrix M.

4. The method of claim 3, further comprising selecting said one or more basis functions that are correlated with said neural recording signal from said complete set of basis functions within said matrix $V_{full}$ by analyzing at least one or more of a percent of unaccounted variance of said neural recording signals in said measurement matrix M and a difference of standard deviations of an error in a beginning portion versus an end portion of said neural recording signals in said measurement matrix M.

5. The method of claim 1, wherein said step of multiplying said weights with said basis functions comprises use of the following equation:

$$m_{denoised} = T\,m = T\,s + T\,n;$$

wherein m represents said neural recording signal, s represents a signal that comprises at least one or more of a neural response signal and an artifact signal, n represents an uncorrelated noise signal, T represents a denoising matrix equal to a first matrix comprising said one or more basis functions multiplied by a transpose of said first matrix, and $m_{denoised}$ represents said denoised neural recording signal.

6. The method of claim 5, further comprising describing said noise signal with a covariance matrix $CD_n = E[n\,n'] = T\,E[n\,n']T' = T\,C_n\,T'$.

7. The method of claim 1, further comprising:
   designating said neural recording signal as including an evoked neural response if an amplitude of said denoised neural recording signal exceeds a confidence interval.

8. The method of claim 1, further comprising determining a minimum amplitude of said stimulus pulse that evokes a neural response signal.

9. The method of claim 1, wherein said neural recording signal corresponds to an auditory nerve.

10. A system for denoising a neural recording signal, said system comprising:
    a neural stimulator configured to generate a neural recording signal by stimulating neural tissue with a stimulus pulse; and
    at least one device in communication with said neural stimulator and configured to
        correlate said neural recording signal with one or more basis functions derived using principal component analysis to produce one or more weights; and
        multiply said weights with said basis functions to obtain a denoised neural recording signal.

11. The system of claim 10, wherein said one or more basis functions comprises at least two basis functions and less than or equal to seven basis functions.

12. The system of claim 10, wherein said at least one device is further configured to:
    designate said neural recording signal as including an evoked neural response if an amplitude of said denoised neural recording signal exceeds a confidence interval.

13. The system of claim 10, wherein said neural stimulator comprises an implantable cochlear stimulator.

14. The system of claim 10, wherein said neural stimulator comprises at least one or more of a spinal cord stimulator, a deep brain stimulator, and a microstimulator.

15. A system for denoising a neural response signal, said system comprising:
    means for applying a stimulus pulse to neural tissue to generate a neural recording signal;
    means for correlating said neural recording signal with one or more basis functions derived using principal component analysis to produce one or more weights; and
    means for multiplying said weights with said basis functions to obtain a denoised neural recording signal.

16. The system of claim 15, wherein said one or more basis functions comprises at least two basis functions and less than or equal to seven basis functions.

17. The system of claim 15, further comprising:
    means for designating said neural recording signal as including an evoked neural response if an amplitude of said denoised neural recording signal exceeds a confidence interval.

18. The system of claim 15, further comprising means for determining a minimum amplitude of said stimulus pulse that evokes said neural response signal.

* * * * *